United States Patent [19]
Elliott et al.

[11] Patent Number: 5,318,814
[45] Date of Patent: Jun. 7, 1994

[54] INHIBITING THE SETTLING OF BARNACLES

[75] Inventors: Sharon J. Elliott, Hempfield Township, Westmoreland County; Virginia Piermattie, Pittsburgh, both of Pa.; Stanley A. Rice, Tampa, Fla.; Theodore R. Wessendorf, Florence, Ky.

[73] Assignee: Aristech Chemical Corporation, Pittsburgh, Pa.

[21] Appl. No.: 43,093

[22] Filed: Apr. 5, 1993

[51] Int. Cl.$^5$ .................. C08F 126/06; C08F 122/04; C08L 33/12; C08L 39/04
[52] U.S. Cl. ........................... 428/36.92; 525/327.6; 526/262
[58] Field of Search ................. 525/327.6; 428/36.92; 526/262

[56] References Cited

U.S. PATENT DOCUMENTS

| | | | |
|---|---|---|---|
| 3,676,404 | 7/1972 | Nield | 260/78 UA |
| 4,111,879 | 9/1978 | Mori et al. | 260/29.6 N |
| 4,696,978 | 9/1987 | Dean | 525/205 |
| 4,701,493 | 10/1987 | Dean | 524/504 |
| 4,983,669 | 1/1991 | Piermattie et al. | 525/47 |

Primary Examiner—James J. Seidleck
Assistant Examiner—I. Zemel
Attorney, Agent, or Firm—William L. Krayer

[57] ABSTRACT

Settlement of barnacles on surfaces in a marine environment is inhibited by employing as a construction material for said surface of polymers including methyl methacrylate and an effective amount (preferably about 2% to about 10%) of a copolymerizable N-substituted maleimide.

6 Claims, 2 Drawing Sheets

INHIBITING THE SETTLING OF BARNACLES

TECHNICAL FIELD

This invention relates to the inhibiting of settling of barnacles on surfaces in a marine environment, through the use, as a structural material, of a composition comprising N-phenyl maleimide or N-cyclohexyl maleimide copolymerized in a matrix of polymethylmethacrylate.

BACKGROUND OF THE INVENTION

It is known from Mori et al U.S. Pat. No. 4,111,879 that resin-based coatings or paints having in them certain amounts of N-phenyl maleimide (hereafter sometimes "NPM") will be effective in reducing the population of barnacles compared to articles submerged in a marine environment and not coated or painted with them. The NPM is not copolymerized with methyl methacrylate or any other monomer; rather, the "resin" is preformed.

NPM has been introduced into unsaturated polyester compositions through copolymerization with the styrene in which the polyester is normally dissolved. See Piermattie et al U.S. Pat. No. 4,983,669. It has also been copolymerized with ABS, styrene, and methyl methacrylate. See Nield U.S. Pat. No. 3,676,404, Dean U.S. Pat. No. 4,696,978, and Dean U.S. Pat. No. 4,701,493. The copolymers described in the Nield and Dean patents are useful in the present invention, and the entire subject matter of them is incorporated herein by reference. However, we are not aware of its use as a comonomer in polymethylmethacrylate to inhibit the settlement of marine organisms.

SUMMARY OF THE INVENTION

Our invention is a method for inhibiting the settlement of marine animals on underwater surfaces. In particular, it provides that marine animals are inhibited from settling on underwater surfaces by constructing said underwater surfaces with polymethylmethacrylate compositions. Some of the economically significant underwater surfaces to which our invention pertains include boat hulls, buoys, and pilings.

DETAILED DESCRIPTION OF THE INVENTION

We have shown that polymethylmethacrylate having incorporated therein as a copolymer at least about 1% N-phenyl maleimide will resist the settlement of barnacles.

Our experiments involved the use of panels four inches square, made of polymethylmethacrylate, with 0%, 2%, 4%, 6%, and 10% NPM which had been made under conditions to assure that the NPM was copolymerized. Specifically, the panels were made by cell casting the formulations made as follows: The base ingredients were 547.2 g methyl methacrylate, 118 g of a methyl methacrylate syrup containing about 25% polymethylmethacrylate, 47.6 g butyl acrylate, 0.64 g poly(ethylene glycol) dimethacrylate as a crosslinking agent, 85.92 g particulate impact modifier, 1.6 g of a commercial release agent, 0.08 g unneutralized fatty alcohol phosphate as an antistatic agent, 0.4 g of a benzotriazole derivative as a UV stabilizer, 0.144 g of t-butylperoxypivalate and 0.896 g t-amylperoxy-2-ethyl hexanoate as a catalyst system. A control was made with no NPM. The various percentages of NPM were made by adding 14.5 g NPM (2%), 29.5 g NPM (4%), 45 g NPM (6%), 62 g NPM (8%), and 80 g NPM (10%). Cure was completed at 84° C. for one hour followed by 121° C. for 29 minutes, whereby the NPM was copolymerized.

Figure 1:
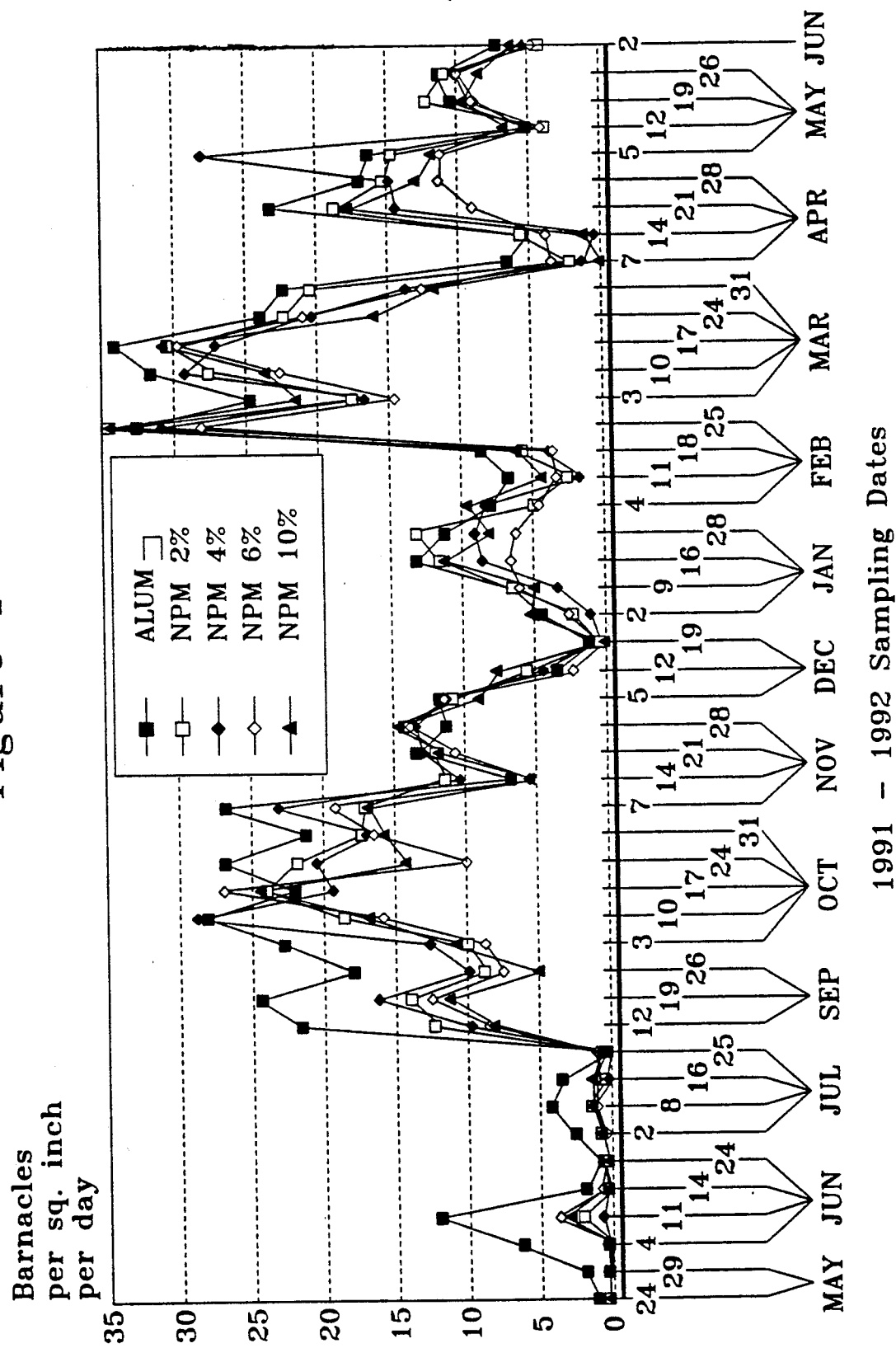
FIG. 1 shows barnacle settlement on aluminum and panels of polymethylmethacrylate having four different strengths of NPM incorporation.

Two to six panels of each strength of NPM were suspended in Tampa Bay at the same depth and at the same time, along with panels of aluminum. They were permitted to collect marine growths for one week, when they were pulled. Barnacles of the species *Balanus eberneus*, the most prolific type of barnacle in the area, were counted and noted in terms of barnacles per square inch. The panels were then scraped to remove all marine growth and returned to the water. One week later they were removed, the barnacles counted as before, and the panels scraped as before and returned to the water. This series of steps was repeated every week for 36 weeks, as noted in FIGS. 1 and 2.

Figure 2:
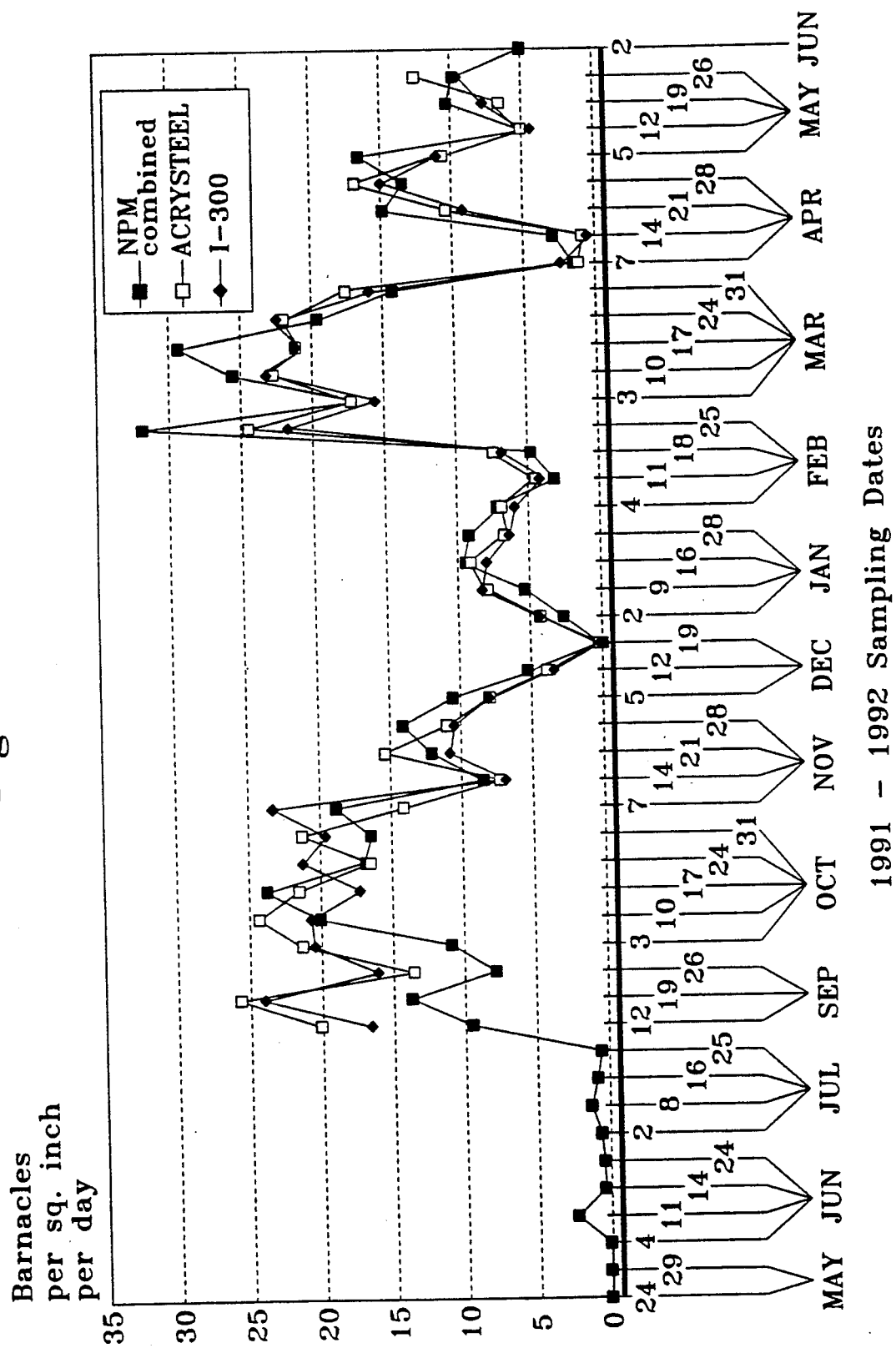
FIG. 2 shows settlement using the same data as FIG. 1 but including also Acrysteel, which is polymethylmethacrylate with no NPM.

It will be noted from FIG. 2 that as compared to the control with no NPM, the panels containing NPM discouraged settlement for as long as 18 weeks.

In analyzing the data, it is necessary to consider several significant effects, notably the temperature of the water and its salinity; the vagaries of salinity are caused by heavy rainfall or the lack of it. An influx of fresh water will adversely affect the propogation of *Balanus eberneus* larvae; likewise the seasonal and other variations in water temperature affect the proliferation of the larvae.

Thus, it may be seen that our invention is a method of inhibiting the settlement of barnacles on a marine surface or article comprising making such surface or article from a polymer comprising methyl methacrylate and an effective amount, preferably at least about 1% and up to about 40% of an N-substituted maleimide wherein the substituent group on the nitrogen is a saturated or unsaturated cyclic group.

We claim:

1. Method of inhibiting the settlement of barnacles on a marine surface or article exposed to settlement thereof comprising making such surface or article from a copolymer including as monomers methyl methacrylate and an effective amount of N-phenyl maleimide, and exposing said surface or article to settlement of barnacles.

2. Method of claim 1 in which such surface or article is a boat hull.

3. Method of claim 1 in which such surface or article is a buoy.

4. Method of claim 1 in which such surface or article is a piling.

5. Method of claim 1 wherein the N-phenyl maleimide comprises about 1% to about 40% of the weight of said copolymer.

6. Method of claim 1 wherein the N-phenyl maleimide comprises about 2% to about 10% of the weight of said copolymer.

* * * * *